US00PP19890P2

(12) United States Plant Patent
Bradford

(10) Patent No.: US PP19,890 P2
(45) Date of Patent: Apr. 7, 2009

(54) NECTARINE TREE NAMED 'SUGARRED II'

(50) Latin Name: *Prunus persica*
Varietal Denomination: Sugarred II

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/003,392

(22) Filed: Dec. 26, 2007

(51) Int. Cl.
*A01H 5/00* (2006.01)

(52) U.S. Cl. ..... Plt./187
(58) Field of Classification Search ..... Plt./187, Plt./190
See application file for complete search history.

(56) References Cited

U.S. PATENT DOCUMENTS

PP7,507 P 4/1991 Bradford
PP15,845 P2 7/2005 Bradford

*Primary Examiner*—Annette H Para
*Assistant Examiner*—June Hwu

(57) ABSTRACT

The present invention relates to a new and distinct variety of nectarine tree, *Prunus persica,* broadly characterized by a medium size, vigorous, hardy, self-fertile, productive and regular bearing tree. The variety blooms somewhat early and requires about 400 chilling hours. The fruit matures under the ecological conditions described in early June, with first picking on Jun. 3, 2007. The fruit is uniformly large in size, acidic and sweet in flavor, globose in shape, clingstone in type, firm and melting in texture, mostly red in flesh color, and mostly red in skin color.

1 Drawing Sheet

Botanical classification: *Prunus persica.*
Variety denomination: 'SUGARRED II'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Sugarred II'.

The present variety was hybridized by me in 1995 as a first generation cross using 'Spring Bright' (U.S. Plant Pat. No. 7,507) nectarine as the selected seed parent and an unnamed low chill peach (unpatented) as the selected pollen parent. The fruit of this cross was gathered that spring, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 1999 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Spring Bright' nectarine by producing nectarines that are firm, mostly red in skin color, clingstone in type, and acidic in flavor, but is quite distinguished therefrom by requiring less chilling hours and by producing fruit that is extremely red instead of yellow in flesh color, that is oblate instead of globose in shape, and that matures about eighteen days earlier.

The present variety is more similar to 'Rose Bright' (U.S. Plant Pat. No. 15,845) nectarine by producing nectarines that are firm in texture, that are acidic and sweet in flavor, that are nearly full red in skin color, and that ripen in early June, but is distinguished therefrom by requiring less chilling hours and by producing fruit that has a much deeper suture at the apex, that is somewhat larger, and that is mostly red instead of yellow in flesh color.

SUMMARY OF VARIETY

In summary, the present variety is characterized by a medium size, vigorous, hardy, self-fertile, productive and regular bearing tree. The variety blooms somewhat early and requires about 400 chilling hours. The fruit matures under the ecological conditions described in early June, with first picking on Jun. 3, 2007. The fruit is uniformly large in size, acidic and sweet in flavor, globose in shape, clingstone in type, firm and melting in texture, mostly red in flesh color, and mostly red in skin color.

DRAWING

The accompanying photograph consists of four whole fruits positioned to display the characteristics of the skin color and form, one sliced fruit to reveal the flesh, two insets to reveal buds and a blossom, characteristic leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 6, 2007, on the original tree during its twelfth growing season. The blossom and flower descriptions were made the previous blooming season. All major color code designations are by reference to the Inter-Society Color Council, National Bureau of Standards. Common color names are also used occasionally.

Parentage

Seed parent: 'Spring Bright' (U.S. Plant Pat. No. 7,507) nectarine.

Pollen parent: Unnamed low chill peach.

Tree

Size: Medium, reaching and maintaining a height of 10' [3.05 m.] and a spread of 9' [2.74 m.] after twelve growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 400 hours.

Trunk:

*Size.*—Medium, reaching a maximum diameter of 6½" [165 mm.] after the twelfth growing season.

*Texture.*—Shaggy.

*Bark color.*—A Moderate yellowish brown [77. m.yBr] and Dark yellowish brown [78. d.yBr] variegation with Strong yellowish brown [74. s.yBr] crevices present.

*Lenticels.*—Approximate Number Per Square Inch: 4. Color: Strong yellowish brown [74. s.yBr]. Average Size: ⅜" [9.5 mm.]. Shape: Eye-shaped, elongated.

Branches:

*Size.*—Diameter of limb is 3¾" [95 mm.] measured 12" above the crotch, 2½" [64 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Grayish yellowish brown [80. gy.yBr].

*Lenticels.*—Number Per Square Inch: More than 40 on second year wood. Color: Light yellowish brown [76. l.yBr]. Average size: 1/32" [0.8 mm.] on second year wood. Shape: Rectangular, elongated.

Leaves:

*Size.*—Large. Average Length: 6⅞" [174.6 mm.]. Average Width: 1 11/16" [42.9 mm.].

*Arrangement.*—Alternate.

*Thickness.*—Medium.

*Form.*—Elliptical.

*Apex.*—Acuminate.

*Base.*—Acute, with an average base angle of 75 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 5/16" [7.9 mm.]. Average Thickness: 1/16" [1.6 mm.]. Color: Strong yellow green [117. s.YG].

*Stipules.*—Number: Usually 2 per leaf, up to 6 per growing tip. Average Length: ¼" [6.4 mm.]. Color: Very yellow green [115. v.YG] becoming Moderate reddish brown [43. m.rBr] with maturity.

*Glands.*—Number: 2 to 4 per leaf. Position: Mostly alternate with a few opposite, located on petiole and base of blade. Size: Small. Form: Globose. Color: Very yellow green [115. v.YG] becoming Deep reddish brown [41. deep rBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.

*Tip color.*—Light purplish pink [249. l.pPk].

Flowers: Perfect, complete, perigynous, usually a single pistil, typically thirty or more stamens, five sepal and petal locations alternately positioned.

*Type.*—Showy, large.

*Average flower diameter.*—2⅛" [54.0 mm.].

*Number of petals.*—Usually five, occasional extra petal fragments, double blossoms rarely observed.

*Petal shape.*—Circular to oval.

*Petal margin.*—Entire, slightly wavy, occasional notches.

*Average petal diameter.*—⅞" [22.2 mm.].

*Average petal length.*—⅞" [22.2 mm.].

*Petal apex.*—Rounded.

*Petal base.*—Rounded to somewhat truncate.

*Petal color.*—Pale pink [7. p.Pk] toward the apex, Pale purplish pink [252. p.pPk] toward the base on both sides.

*Anther color.*—Light orange [52. l.O] over a Light yellow [86. l.Y] center at bloom onset.

*Stigma color.*—Pale yellow green [121. p.YG].

*Sepal color.*—Dark purplish red [259. d.pR] on the outer surface.

*Sepal length.*—¼" [6.4 mm.].

*Sepal width.*—3/16" [4.8 mm.].

*Sepal apex.*—Rounded to elliptical to match the sepal length and width.

*Sepal margin.*—Fairly smooth.

*Average pistil length.*—13/16" [20.6 mm.].

*Average stamen length.*—⅝" [15.9 mm.].

*Fragrance.*—Moderate.

*Blooming period.*—Somewhat early, one week before 'Spring Bright' (U.S. Plant Pat. No. 7,507) nectarine.
*Onset of bloom.*—One percent on Feb. 23, 2007.
*Date of full bloom.*—Mar. 4, 2007.
*Duration of bloom.*—One to two weeks, dependent on ambient temperature.
*Number per cluster.*—1 to 3 with single flowers most common.

FRUIT

Maturity when described: Firm ripe, Jun. 6, 2007.
Date of first picking: Jun. 2, 2007.
Date of last picking: Jun. 12, 2007.
Size: Uniform, large.
*Average diameter axially.*—2 11/16" [68.3 mm.].
*Average diameter across cheek plane.*—3" [76.2 mm.].
*Average diameter across suture plane.*—2 7/8" [73.0 mm.].
*Typical weight.*—7.0 ounces [198 grams].
Form: Globose, slightly asymmetrical.
*Longitudinal section form.*—Round to elliptical.
*Transverse section through diameter.*—Round to elliptical.
Suture: Extends from the base, along the side and past the pistil point.
*Near the base.*—A sharp groove.
*Along the side.*—A broadened trough.
*Near the apex.*—A deep and sharp groove.
Ventral surface: Rounded, lipped throughout, but very strongly toward the apex.
Lips: Mostly equal.
Cavity: Flaring, elongated in the suture plane, suture showing on one side, Very greenish yellow [97. v.gY] stem markings typical.
*Depth.*—9/16" [14.3 mm.].
*Breadth.*—1 1/8" [28.6 mm.].
Base: Rounded to somewhat truncate.
Apex: Rounded, but strongly cordate if viewed parallel to the suture.
Pistil point: Apical, negligible in length, depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—Slight in wet season.
*Color.*—Dark red [16. d.R] over a Moderate reddish orange [37. m.rO] background with Pale orange yellow [73. p.OY] freckling toward the apex.
Flesh:
*Color.*—Brilliant orange yellow [67. brill.OY] with Very red [11. v.R] streaking and bleeding throughout.
*Surface of pit cavity.*—Covered with Dark red [16. d.R] broken fibers when twisted from the stone.
*Amygdalin.*—Abundant to moderate.
*Juice.*—Moderate, rich.
*Texture.*—Firm, crisp.
*Fibers.*—Abundant, fine, tender.
*Ripens.*—Slightly earlier at the apex.
*Flavor.*—Acidic and sweet, typically 14 brix.
*Aroma.*—Moderate.
*Eating quality.*—Very good.

STONE

Type: Clingstone.
Form: Oval.
Hilum: Narrow, oval.
Base: Straight.
Apex: Acuminate, with a 1/16" [1.6 mm.] tip having an average tip angle of 75 degrees.
Sides: Equal.
Surface: Regularly furrowed near the apex and along the ventral edge, pitted stronger toward the base.
Ridges: Rounded.
External color: Moderate yellowish brown [77. m.yBr].
Pit wall color when cracked: Light yellowish brown [76. l.yBr].
Cavity surface color: Strong yellowish brown [74. s.yBr].
Average pit wall thickness: 1/4" [6.4 mm.].
Average width: 1 1/8" [28.6 mm.].
Average length: 1 9/16" [39.7 mm.].
Average breadth: 1 1/16" [27.0 mm.].
Tendency to split: Slight.
Kernel:
*Form.*—Oval.
*Skin color.*—Strong yellowish brown [74. s.yBr].
*Pellicle color.*—Deep yellowish brown [75. deep yBr].
*Vein color.*—Moderate yellowish brown [77. m.yBr].
*Taste.*—Sweet.
*Viable.*—Only by using embryo rescue.
*Average width.*—1/2" [12.7 mm.].
*Average length.*—13/16" [20.6 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is similar to 'Rose Bright' (U.S. Plant Pat. No. 15,845) nectarine by producing nectarines that are firm in texture, that are acidic and sweet in flavor, that are nearly full red in skin color, and that ripen in early June, but is distinguished therefrom by requiring less chilling hours and by producing fruit that has a much deeper suture at the apex, that is somewhat larger, and that is mostly red instead of yellow in flesh color.

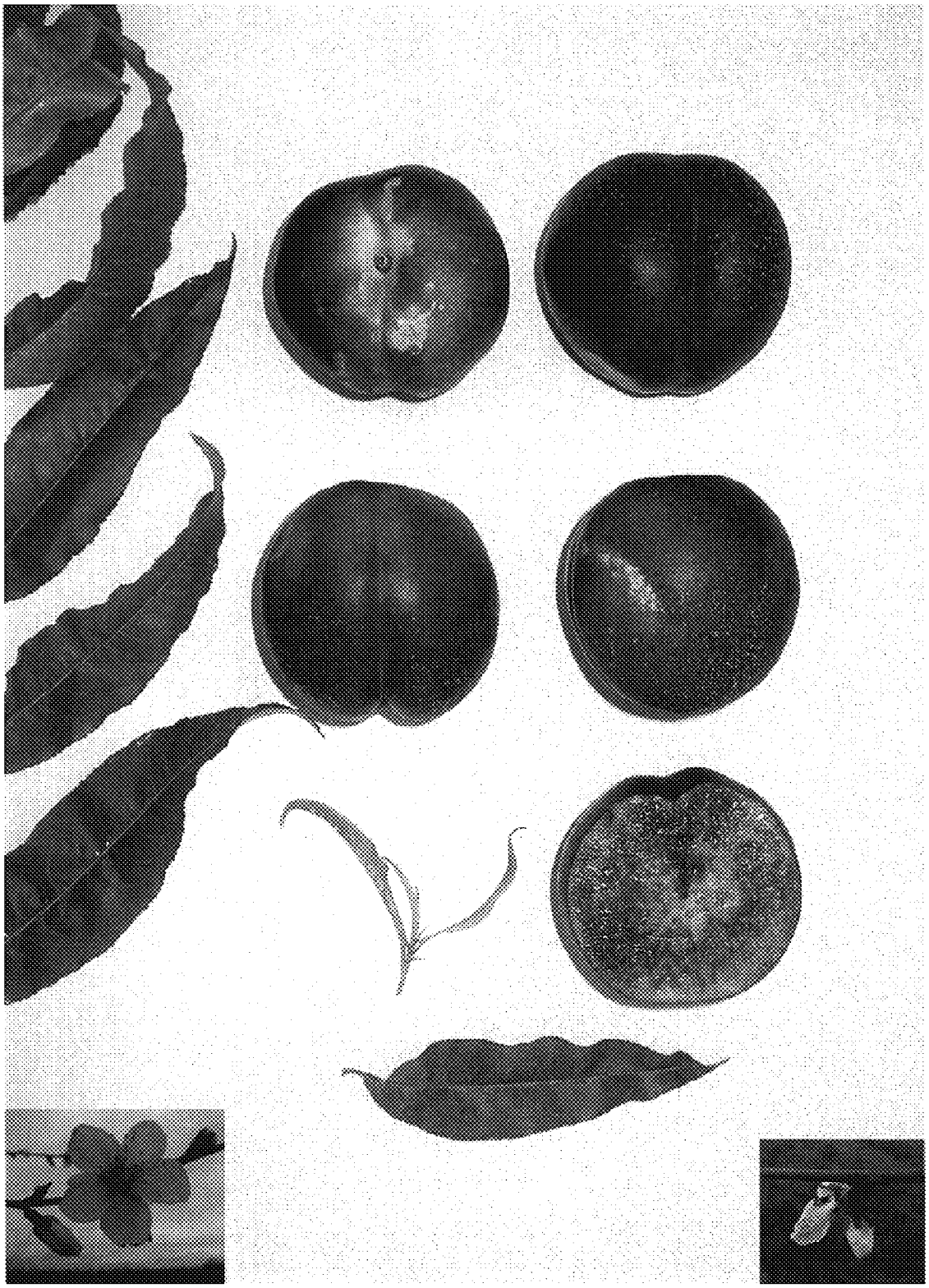

* * * * *